United States Patent [19]

Rentzea et al.

[11] 4,071,685
[45] Jan. 31, 1978

[54] 1-ALKYLCARBAMOYL-3-(3,5-DICHLORO-PHENYL)-HYDANTOINS

[75] Inventors: Costin Rentzea, Heidelberg; Bernd Zeeh, Ludwigshafen; Karl-Heinz Koenig, Frankenthal; Ernst-Heinrich Pommer, Limburgerhof, all of Germany

[73] Assignee: BASF Aktiengesellschaft, Ludwigshafen (Rhine), Germany

[21] Appl. No.: 725,843

[22] Filed: Sept. 23, 1976

[30] Foreign Application Priority Data

Nov. 13, 1975 Germany .............................. 2550964

[51] Int. Cl.$^2$ ............................................ C07D 233/90
[52] U.S. Cl. ................................ 548/312; 424/273 R
[58] Field of Search ...................... 260/309.5; 424/273

[56] References Cited

U.S. PATENT DOCUMENTS 3,716,552  2/1973  Fujinami et al. ................... 260/309.5
3,755,350  8/1973  Sauli ................................. 260/309.5

OTHER PUBLICATIONS

Lacroix et al., Chem. Abst. 1975, vol. 83, No.2032z.
Jones Chem. Abst. 1975, vol. 83, No. 38622f.

*Primary Examiner*—Natalie Trousof
*Attorney, Agent, or Firm*—Keil, Thompson & Shurtleff

[57] ABSTRACT

1-Alkylcarbamoyl-3-(3,5-dichlorophenyl)-hydantoins and a method of combatting unwanted phytopathogenic fungi with these compounds.

11 Claims, No Drawings

1-ALKYLCARBAMOYL-3-(3,5-DICHLOROPHENYL)-HYDANTOINS

The present invention relates to new and valuable 1-alkylcarbamoyl-3-(3,5-dichlorophenyl)-hydantoins, fungicides containing these compounds, and a method of combatting unwanted phytopathogenic fungi with these compounds.

It is known (German Laid-Open Application DOS No. 2,149,923) to use hydantoin derivatives, for instance 1-isopropylcarbamoyl-3-(3,5-dichlorophenyl)-hydantoin, as fungicides in agriculture. However, they do not meet all the demands placed on them in practice.

We have now found that new hydantoin derivatives of the general formula

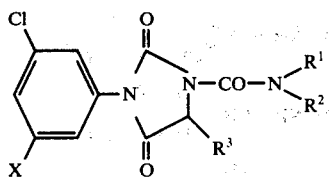

where $R^1$ denotes halogen-substituted, alkylmercapto-substituted or alkoxy-substituted linear or branched alkyl of 2 to 5 carbon atoms, haloalkenyl of 3 carbon atoms, alkynyl of 4 to 8 carbon atoms, tetrahydropyranyl, unsubstituted or halogen-substituted, alkyl-substituted or alkoxy-substituted cycloalkyl of 3 to 6 carbon atoms in the cycloalkyl ring; $R^2$ denotes hydrogen or, when $R^1$ is methyl, ethyl, isopropyl or cyclohexyl, methoxy; $R^3$ denotes hydrogen or methyl; and X denotes chloro or bromo, have a better fungicidal action than prior art hydantoin derivatives. The compounds of the invention are particularly suitable for protecting plants against *Erysiphe graminis, Botrytis cinerea, Alternaria solani, Monilia spec., Sclerotinia sclerotiorum* and *Rhizoctonia solani*. To combat phytopathogenic fungi, the compounds of the invention should be used in amounts of from 0.25 to 2.5 kg per hectare.

Due to the excellent persistence of the new active ingredients on the plants it is possible to increase the intervals between fungicide treatments, i.e., to reduce the number of fungicide applications necessary to protect the plants against new fungus infections.

The active ingredients according to the invention may be prepared by reaction of 3-(3,5-dichlorophenyl)-hydantoin synthesized by known methods (e.g. C. Runti and F. Ulian, Ann. Chim., 55, 845, 1965; D. Pressman and coworkers, J. Am. Chem. Soc., 70, 1352, 1948; and A. Mouneyrat, Chem. Ber., 33, 2393, 1900) with haloalkyl, haloalkenyl, alkynyl, alkoxyalkyl, mercaptoalkyl or cycloalkyl isocyanates of the formula $R^1$-NCO, or with carbamyl chlorides of the formula

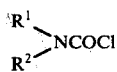

and an acid-binding agent.

The following compounds are examples of active ingredients according to the invention:

1-(2-chloroethylcarbamoyl)-3-(3,5-dichlorophenyl)-hydantoin
1-(2-chloropropyl-(1)-carbamoyl)-3-(3,5-dichlorophenyl)-hydantoin
1-(1-chloroisopropylcarbamoyl)-3-(3,5-dichlorophenyl)-hydantoin
1-(1-chlorobutyl-(2)-carbamoyl)-3-(3,5-dichlorophenyl)-hydantoin
1-(1,1-dimethyl-2-chloroethyl-(1)-carbamoyl)-3-(3,5-dichlorophenyl)-hydantoin
1-(1,1-dimethyl-3-chloropropyl-(1)-carbamoyl)-3-(3,5-dichlorophenyl)-hydantoin
1-(1,3-dichloro-2-chloromethylpropyl-(2)-carbamoyl)-3-(3,5-dichlorophenyl)-hydantoin
1-(1-chloroisopropylcarbamoyl)-3-(3-bromo-5-chlorophenyl)-hydantoin
1-(1-chloroisopropylcarbamoyl)-2-methyl-3-(3,5-dichlorophenyl)-hydantoin
1-(1-chlorobutyl-(2)-carbamoyl)-2-methyl-3-(3,5-dichlorophenyl)-hydantoin
1-(1-methylmercaptoisopropylcarbamoyl)-2-methyl-3-(3,5-dichloro-phenyl)-hydantoin
1-(N-methoxy-N-isopropylcarbamoyl)-2-methyl-3-(3,5-dichlorophenyl)-hydantoin
1-methoxymethylcarbamoyl-3-(3,5-dichlorophenyl)-hydantoin
1-(1-methoxyisopropylcarbamoyl)-3-(3,5-dichlorophenyl)-hydantoin
1-(2-tetrahydropyranylcarbamoyl)-3-(3,5-dichlorophenyl)-hydantoin
1-(2-methylmercaptoethylcarbamoyl)-3-(3,5-dichlorophenyl)-hydantoin
1-(2-ethylmercaptoethylcarbamoyl)-3-(3,5-dichlorophenyl)-hydantoin
1-(1-methylmercaptoisopropylcarbamoyl)-3-(3,5-dichlorophenyl)-hydantoin
1-(1-ethylmercaptoisopropylcarbamoyl)-3-(3,5-dichlorophenyl)-hydantoin
1-(1-n-propylmercaptoisopropylcarbamoyl)-3-(3,5-dichlorophenyl)-hydantoin
1-(1-methylmercaptobutyl-(2)-carbamoyl)-3-(3,5-dichlorophenyl)-hydantoin
1-(1-ethylmercaptobutyl-(2)-carbamoyl)-3-(3,5-dichlorophenyl)-hydantoin
1-(1,1-dimethyl-2-methylmercaptoethyl-(1)-carbamoyl)-3-(3,5-dichlorophenyl)-hydantoin
1-(1,1-dimethyl-2-ethylmercaptoethyl-(1)-carbamoyl)-3-(3,5-dichlorophenyl)-hydantoin
1-(2-ethynylisopropylcarbamoyl)-3-(3,5-dichlorophenyl)-hydantoin
1-(2-ethynylbutyl-(2)-carbamoyl)-3-(3,5-dichlorophenyl)-hydantoin
1-(N-methoxy-N-methylcarbamoyl)-3-(3,5-dichlorophenyl)-hydantoin
1-(N-methoxy-N-isopropylcarbamoyl)-3-(3,5-dichlorophenyl)-hydantoin
1-(N-methoxy-N-cyclohexylcarbamoyl)-3-(3,5-dichlorophenyl)-hydantoin
1-cyclopropylcarbamoyl-3-(3,5-dichlorophenyl)-hydantoin
1-(1-cyclopropylethyl-(1)-carbamoyl)-3-(3,5-dichlorophenyl)-hydantoin
1-cyclopentylcarbamoyl-3-(3,5-dichlorophenyl)-hydantoin
1-cyclohexylcarbamoyl-3-(3,5-dichlorophenyl)-hydantoin
1-(2,4-dimethylcyclohexylcarbamoyl)-3-(3,5-dichlorophenyl)-hydantoin
1-(3,5-dimethylcyclohexylcarbamoyl)-3-(3,5-dichlorophenyl)-hydantoin
1-(4-methoxycyclohexylcarbamoyl)-3-(3,5-dichlorophenyl)-hydantoin 1-(2-trifluoromethylcyclohexylcarbamoyl)-3-(3,5-dichlorophenyl)-hydantoin 1-(1-ethynylcyclohexylcarbamoyl)-3-(3,5-dichlorophenyl)-hydantoin The preparation of the active ingredients is illustrated below.

EXAMPLE 1

1-(1-chloroisopropylcarbamoyl)-3-(3,5-dichlorophenyl)-hydantoin

At about 20° C and with vigorous stirring, 4 parts (by weight) of triethylamine and subsequently 18 parts of 1-chloro-2-propyl isocyanate are added to a suspension of 24.5 parts of 3-(3,5-dichlorophenyl)-hydantoin in 250 parts of dry acetone. The mixture is heated in the course of an hour to 56° C, whereupon a clear solution forms. After refluxing for 3½ hours the reaction is complete. After the mixture has been cooled to 20° C, n-pentane is added (about 50 parts) until it becomes slightly cloudy; the mixture is then stirred for about 5 minutes with 4 parts of animal charcoal. The mixture is then filtered and concentrated in vacuo, and the residue is washed with petroleum ether and dried. There is obtained 32 parts of analytically pure 1-(1-chloroisopropylcarbamoyl)-3-(3,5-dichlorophenyl)-hydantoin having a melting point of from 96° to 98° C (compound no. 1).

The following compounds were obtained analogously:

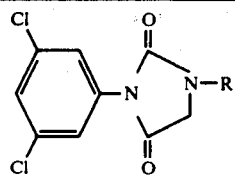

| Compound no. | R | m.p. (° C) |
|---|---|---|
| 2 | —CO—NH—CH₂—CH₂—Cl | 162-163 |
| 3 | —CO—NH—CH(CH₂Cl)(CH₂—CH₃) | 109-110 |
| 4 | —CO—NH—CH₂—CH(Cl)—CH₃ | 97-99 |
| 5 | —CO—NH—C(CCl₂)(CHCl₂) | 181-183 |
| 6 | —CO—NH—C(CH₃)(CH₃)—CH₂—Cl | 148-149 |
| 7 | —CO—NH—C(CH₃)(CH₃)—CH₂—CH₂—Cl | 133-135 |
| 8 | —CO—NH—C(CH₂—Cl)(CH₂—Cl)—CH₂—Cl | 129-132 |
| 9 | —CO—NH—CH₂—O—CH₃ | 168-169 |
| 10 | —CO—NH—CH(CH₃)(CH₂—O—CH₃) | 101-102 |
| 11 | —CO—NH—(tetrahydropyranyl) | 113-115 |
| 12 | —CO—NH—CH₂—CH₂—S—CH₃ | 109-114 |
| 13 | —CO—NH—CH₂—CH₂—S—C₂H₅ | 113-115 |
| 14 | —CO—NH—CH(CH₃)(CH₂—S—CH₃) | 73-75 |
| 15 | —CO—NH—CH(CH₃)(CH₂—S—C₂H₅) | 80-82 |
| 16 | —CO—NH—CH(CH₃)(CH₂—S—C₃H₇-n) | oil |
| 17 | —CO—NH—CH(CH₂—CH₃)(CH₂—S—CH₃) | 65-69 |
| 18 | —CO—NH—CH(CH₂—CH₃)(CH₂—S—C₂H₅) | oil |
| 19 | —CO—NH—C(CH₃)(CH₃)—CH₂—S—CH₃ | oil |
| 20 | —CO—NH—C(CH₃)(CH₃)—CH₂—S—C₂H₅ | 100-102 |
| 21 | —CO—NH—C(CH₃)(CH₃)—C≡CH | 107-108 |
| 22 | —CO—NH—C(CH₃)(C₂H₅)—C≡CH | 96-98 |
| 23 | —CO—NH—(cyclopropyl) | 181-182 |
| 24 | —CO—NH—CH(CH₃)(cyclopropyl) | 129-130 |
| 25 | —CO—NH—(cyclopentyl) | 116-117 |
| 26 | —CO—NH—(cyclohexyl) | 142-144 |
| 27 | —CO—NH—(4-methylcyclohexyl) | 139-141 |
| 28 | —CO—NH—(3,5-dimethylcyclohexyl) | 193-194 |
| 29 | —CO—NH—(4-methoxycyclohexyl) | 107-109 |

-continued

| Compound no. | R | m.p. (° C) |
|---|---|---|
| 30 | —CO—NH—(4-CF₃-cyclohexyl, H) | 174–176 |
| 31 | —CO—NH—(4-C≡CH-cyclohexyl, H) | 107–110 |

(Structure shown: 1-(3,5-dichlorophenyl)-hydantoin with N—R substituent)

EXAMPLE 32

1-(N-methoxy-N-methylcarbamoyl)-3-(3,5-dichlorophenyl)-hydantoin

At about 20° C, 10.5 parts of triethylamine and subsequently 12.4 parts of methylmethoxycarbamoyl chloride are added to a suspension of 24.5 parts of 3-(3,5-dichlorophenyl)-hydantoin in 250 parts of dry tetrahydrofuran. After all has been added, the mixture is refluxed for 3 hours. After the mixture has been cooled to 20° C, the precipitated triethylamine hydrochloride is removed by suction filtration. The filtrate is concentrated. The residue is dissolved in a 1:1 mixture of n-pentane and ether, suction filtered, dried and recrystallized from toluene.

There is obtained 21 parts of pure product (compound no. 32) having a melting point of 179° to 180° C.

The following compounds are obtained analogously:

Compound no. 33 1-(N-methoxy-N-isopropylcarbamoyl)-3-(3,5-dichlorophenyl)-hydantoin, m.p. 136° – 137° C Compound no. 34 1-(N-methoxy-N-cyclohexylcarbamoyl)-3-(3,5-dichlorophenyl)-hydantoin Compound no. 34 1-(1-chloroisopropylcarbamoyl)-3-(3-bromo-5-chlorophenyl)-hydantoin, m.p. 103° – 105° C Compound no. 36 1-(1-chloroisopropylcarbamoyl)-2-methyl-3-(3,5-dichlorophenyl)-hydantoin, m.p. 110° – 112° C Compound no. 37 1-(1-chlorobutyl-(2)-carbamoyl)-2-methyl-3-(3,5-dichlorophenyl)-hydantoin, m.p. 84° – 86° C Compound no. 38 1-(1-methylmercaptoisopropylcarbamoyl)-methyl-3-(3,5-dichlorophenyl)-hydantoin; colorless resin Calculated for $C_{15}H_{17}N_3O_3Cl_2S$:

|  | C | H | N | Cl | S |
|---|---|---|---|---|---|
| calc.: | 50.3% | 4.8% | 11.7% | 19.8% | 8.9% |
| found: | 51.0% | 5.1% | 11.3% | 19.5% | 8.7% |

The structure of this compound was confirmed by the infrared spectrum. The infrared spectrum (in KBr) has the following characteristic absorptions: 3080, 2960, 2920, 2850, 1735, 1590, 1575, 1535, 1453, 1395, 1347, 1265, 1228, 1185, 1147, 1110, 860, 810, 790, 770 and 670 cm$^{-1}$.

Compound no. 39 1-(N-methoxy-N-isopropylcarbamoyl)-2-methyl-3-(3,5-dichlorophenyl)-hydantoin, m.p. 135° – 136° C.

The active ingredients according to the invention may be converted into the usual formulations such as solutions, emulsions, suspensions, powders, pastes and granules. The formulations are prepared in known manner, e.g., by mixing the active ingredient with solvents and/or carriers, if desired with emulsifiers and dispersants; when water is used as diluent other organic solvents may also be employed as auxiliary solvents. The most suitable auxiliaries are solvents, such as aromatics (e.g., xylene, benzene), chlorinated aromatics (e.g., chlorobenzenes), paraffins (e.g., petroleum fractions), alcohols (e.g., methanol, butanol), amines (e.g., ethanolamine, dimethylformamide) and water; carriers, such as natural rock flours (e.g., kaolins, clays, talc, chalk) and synthetic rock flours (e.g., highly disperse silicic acid, silicates); emulsifying agents, such as non-ionogenic and anionic emulsifiers (e.g., polyoxyethylene fatty alcohol ethers, alkyl sulfonates and aryl sulfonates); and dispersants such as lignin, sulfite waste liquors and methyl cellulose.

The formulations generally contain from 0.1 to 95, preferably from 0.5 to 90, wt% of active ingredient. The formulations, or the ready-for-use preparations made therefrom, such as solutions, emulsions, suspensions, powders, pastes and granules, are applied in known manner, e.g., by spraying, atomizing, dusting, broadcasting or watering. The fungi or the plants to be protected against fungus attack are treated with the active ingredients.

The agents according to the invention may also be applied in admixture with other active ingredients, e.g., herbicides, insecticides, growth regulators and fungicides, and also with fertilizers. Examples of fungicides which may be combined with the compounds of the invention are dithiocarbamates and derivatives thereof, e.g.,
ferric dimethyldithiocarbamate
zinc dimethyldithiocarbamate
manganese ethylenebisdithiocarbamate
zinc ethylenebisdithiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene-bisdithiocarbamate) and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide nitrophenol derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate heterocyclic structures, such as
N-trichloromethylthiotetrahydrophthalimide
N-trichloromethylthiophthalimide
2-heptadecyl-2-imidazoline acetate
2,4-dichloro-6-(o-chloroanilino)-s-triazine
O,O-diethylphthalimidophosphonothioate
5-amino-1-[bis-(dimethylamino)-phosphynyl]-3-phenyl-1,2,4-triazole
5-ethoxy-3-trichloromethyl-1,2,4-thiadiazole 2,3-dicyano-1,4-dithiaanthraquinone
2-thio-1,3-dithio-[4,5-b]-quinoxaline
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
pyridine-2-thiol-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
N-dichlorofluoromethylthio-N',N'-dimethyl-N-phenylsulfuric acid diamide
2,6-dimethyl-N-tridecylmorpholine and its salts
2,6-dimethyl-N-cyclododecylmorpholine and its salts
2,5-dimethylfuran-3-carboxylic acid anilide
2,5-dimethylfuran-3-carboxylic acid cyclohexyl amide
2-methylbenzoic acid anilide
2-iodobenzoic acid anilide
1-(3,4-dichloroanilino)-1-formylamino-2,2,2-trichloroethane
2,3-dichloro-1,4-naphthoquinone
2-thiocyanomethylthiobenzothiazole
1,4-dichloro-2,5-dimethoxybenzene
p-dimethylaminobenzenediazosodium sulfonate
2-chloro-1-nitropropane
polychloronitrobenzenes, such as pentachloronitrobenzene,
methyl isothiocyanate, fungicidal antibiotics such as griseofulvin and kasugamycin, tetrafluorodichloroacetone,
1-phenylthio semicarbazide, Bordeaux mixture, nickel-containing compounds and sulfur.

EXAMPLE 40

Begonia cuttings possessing 5 well developed leaves are sprayed to runoff with 0.05 and 0.025% (wt%) aqueous spray liquors containing (dry basis) 80% of active ingredient and 20% of sodium lignin sulfonate. After the sprayed layer has dried, the plants are left for 10 days in a greenhouse at from 20° to 22° C and a relative humidity of from 60 to 70%, and are then sprayed with a suspension containing spores of the fungus Botrytis cinerea. The artificially infected plants are then placed in a chamber having a high humidity and a temperature of from 24° to 26° C, in order to create optimum conditions for disease development. After 5 days the disease has developed to such an extent on the untreated control plants that the necroses cover the major portion of the total leaf surface.

| | Botrytis cinerea in begonias Leaf attack 5 days after infection Plants sprayed with liquor containing | |
|---|---|---|
| Compound no. | 0.05% of active ingredient preparation | 0.025% of active ingredient preparation |
| 1 | 1 | 2 |
| 2 | 2 | 2 |
| 3 | 2 | 2 |
| 11 | 2 | 3 |
| 14 | 2 | 3 |
| 21 | 1 | 3 |
| 22 | 2 | 3 |
| 25 | 2 | 2 |
| (art compound) | 3 | 4 |
| Untreated (control) | 5 | 5 |

1 = isolated necroses
2 = a few necroses
3 = numerous necroses
4 = more than 50% of leaf surface attacked
5 = leaves completely covered

EXAMPLE 41

Leaves of barley seedlings grown in pots are sprayed with 0.1% aqueous solutions (containing (dry basis) 80 wt% of active ingredient and 20 wt% of emulsifier), and dusted with spores of barley mildew (Erysiphe graminis var. hordei) after the sprayed layer has dried. The plants are then placed in a greenhouse having a temperature of from 20° to 22° C and a relative humidity of from 75 to 80%. After 10 days the extent of fungus spread is ascertained.

| Compound no. | Erysiphe graminis in barley Leaf attack after spraying with liquor containing 0.1% of active ingredient preparation |
|---|---|
| 1 | 2 |
| 11 | 2 |
| 21 | 2 |
| 22 | 0 |
| (art compound) | 5 |
| Untreated (control) | 5 |

EXAMPLE 42

90 parts by weight of compound 1 is mixed with 10 parts by weight of N-methyl-α-pyrrolidone. A mixture is obtained which is suitable for application in the form of very fine drops.

EXAMPLE 43

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 44

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 45

20 parts by weight of compound 4 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 46

20 parts by weight of compound 5 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 47

3 parts by weight of compound 6 is intimately mixed with 97 parts by weight of particulate kaolin. A dust is obtained containing 3% by weight of the active ingredient.

EXAMPLE 48

30 parts by weight of compound 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 49

40 parts by weight of compound 8 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 50

20 parts of compound 9 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A hydantoin derivative of the formula

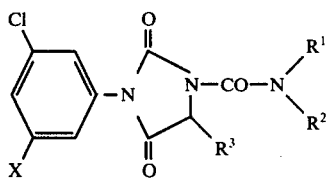

where $R^1$ denotes halogen-substituted, alkylmercapto-substituted or alkoxy-substituted linear or branched alkyl of 2 to 5 carbon atoms, haloalkenyl of 3 carbon atoms, alkynyl of 4 to 8 carbon atoms, tetrahydropyranyl, unsubstituted or halogen-substituted, alkyl-substituted or alkoxy-substituted cycloalkyl of 3 to 6 carbon atoms in the cycloalkyl ring, in which case $R^2$ denotes hydrogen; or $R^1$ denotes methyl, ethyl, isopropyl or cyclohexyl, in which case $R^2$ denotes methoxy; $R^3$ denotes hydrogen or methyl; and X denotes chloro or bromo.

2. A hydantoin derivative as claimed in claim 1, wherein $R^2$ denotes hydrogen and $R^1$ denotes halogen-substituted, alkylmercapto-substituted or alkoxy-substituted linear or branched alkyl of 2 to 5 carbon atoms, haloalkenyl of 3 carbon atoms, alkynyl of 4 to 8 carbon atoms, tetrahydropyranyl, unsubstituted or halogen-substituted, alkyl-substituted or alkoxy-substituted cycloalkyl of 3 to 6 carbon atoms in the cycloalkyl ring.

3. A hydantoin derivative as claimed in claim 1, wherein $R^2$ denotes methoxy, and $R^1$ denotes methyl, ethyl, isopropyl or cyclohexyl.

4. 1-(1-chloroisopropylcarbamoyl)-3-(3,5-dichlorophenyl)-hydantoin.

5. 1-(2-chloroethylcarbamoyl)-3-(3,5-dichlorophenyl)-hydantoin.

6. 1-(1-chlorobutyl-(2)-carbamoyl)-3-(3,5-dichlorophenyl)-hydantoin.

7. 1-(2-tetrahydropyranylcarbamoyl)-3-(3,5-dichlorophenyl)-hydantoin.

8. 1-(1-methylmercaptoisopropylcarbamoyl)-3-(3,5-dichlorophenyl)-hydantoin.

9. 1-(2-ethynylisopropylcarbamoyl)-3-(3,5-dichlorophenyl)-hydantoin.

10. 1-(2-ethynylbutyl-(2)-carbamoyl)-3-(3,5-dichlorophenyl)-hydantoin.

11. 1-cyclopentylcarbamoyl-3-(3,5-dichlorophenyl)-hydantoin.

* * * * *